US007674236B2

(12) United States Patent
Daniel et al.

(10) Patent No.: US 7,674,236 B2
(45) Date of Patent: Mar. 9, 2010

(54) DEVICE AND METHOD FOR DETECTING COMPLICATIONS DURING AN EXTRACORPOREAL BLOOD TREATMENT

(75) Inventors: Pia Daniel, Bodmann (DE); Carsten Müller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 11/794,971

(22) PCT Filed: Oct. 15, 2005

(86) PCT No.: PCT/EP2005/011103

§ 371 (c)(1), (2), (4) Date: Jul. 9, 2007

(87) PCT Pub. No.: WO2006/072271

PCT Pub. Date: Jul. 13, 2006

(65) Prior Publication Data

US 2008/0097272 A1 Apr. 24, 2008

(30) Foreign Application Priority Data

Jan. 7, 2005 (DE) .................. 10 2005 001 051

(51) Int. Cl.
*A61M 37/00* (2006.01)
*B01D 61/00* (2006.01)
*C02F 1/00* (2006.01)

(52) U.S. Cl. .............. 604/6.09; 210/739; 210/740; 210/741; 210/742; 210/743; 210/645; 210/646; 604/4.01; 604/5.01; 604/6.06; 604/5.04

(58) Field of Classification Search ........... 604/6.06, 604/6.09, 4.01, 5.01; 600/371, 372; 210/645, 210/646, 739, 742, 744, 746
See application file for complete search history.

(56) References Cited

U.S. PATENT DOCUMENTS 4,897,184 A * 1/1990 Shouldice et al. .......... 210/87

(Continued)

FOREIGN PATENT DOCUMENTS

DE 195 28 907 11/1995

(Continued)

OTHER PUBLICATIONS

International Search Report (ISR) from PCT/EP2005/011103.

(Continued)

*Primary Examiner*—Tatyana Zalukaeva
*Assistant Examiner*—Susan Su
(74) *Attorney, Agent, or Firm*—Kenyon & Kenyon LLP

(57) ABSTRACT

A device and method for detecting complications during an extracorporeal blood treatment are provided. During the dialysis treatment, the dialysance or clearance may be continuously determined at successive points in time based on a measured change in a physical or chemical characteristic quantity of the dialysis liquid, for example, the ion concentration of the dialysis liquid. In the event a significant change in the dialysance or clearance is established, the determination of the recirculation may be effected based on a measured change in a physical or chemical characteristic quantity of the blood. When both a significant change in the determined dialysance as well as in the recirculation occurs, a complication may be assumed with regard to a bad vessel access. Alternatively, a complication may be assumed with regard to the dialyzer. The present invention may allow the continuous monitoring during the dialysis treatment to ensue solely on the basis of the change in the measured dialysate-side characteristic quantities.

14 Claims, 2 Drawing Sheets

U.S. PATENT DOCUMENTS

| | | | |
|---|---|---|---|
| 5,312,550 A * | 5/1994 | Hester | 210/646 |
| 5,588,959 A | 12/1996 | Ahmad et al. | |
| 5,744,031 A * | 4/1998 | Bene | 210/321.71 |
| 5,830,365 A * | 11/1998 | Schneditz | 210/739 |
| 5,866,015 A | 2/1999 | Krämer | |
| 6,156,002 A * | 12/2000 | Polaschegg et al. | 604/4.01 |
| 6,706,007 B2 * | 3/2004 | Gelfand et al. | 604/4.01 |
| 6,796,955 B2 * | 9/2004 | O'Mahony et al. | 604/6.11 |
| 6,861,266 B1 * | 3/2005 | Sternby | 436/178 |
| 6,868,739 B1 * | 3/2005 | Krivitski et al. | 73/861.05 |
| 7,608,053 B2 * | 10/2009 | Felt et al. | 604/6.05 |
| 2002/0009385 A1 * | 1/2002 | Krivitski et al. | 422/44 |
| 2002/0085952 A1 * | 7/2002 | Ellingboe et al. | 422/45 |
| 2004/0158190 A1 * | 8/2004 | Duchamp et al. | 604/6.09 |
| 2006/0116624 A1 * | 6/2006 | Sternby | 604/5.01 |

FOREIGN PATENT DOCUMENTS

| | | |
|---|---|---|
| DE | 197 47 360 A1 | 12/1996 |
| DE | 195 41 783 | 3/1997 |
| DE | 197 02 441 C1 | 2/1998 |
| DE | 197 39 100 C1 | 2/1999 |

OTHER PUBLICATIONS

Gotch, Frank A., "Models to Predict Recirculation and Its Effect on Treatment Time in Single-Needle Dialysis." *First International Symposium on Single-Needle Dialysis*, edited by S. Ringoir, R. Vanholder, P. Ivanovich, ISAO Press, Cleveland 1984, pp. 47-62.

* cited by examiner

DEVICE AND METHOD FOR DETECTING COMPLICATIONS DURING AN EXTRACORPOREAL BLOOD TREATMENT

FIELD OF THE INVENTION

The present invention relates to a device for detecting complications during an extracorporeal blood treatment with a blood treatment apparatus, wherein the blood to be treated flows in an extracorporeal blood circuit through the blood chamber of a dialyser divided by a semipermeable membrane into the blood chamber and a dialysing fluid chamber and dialysing fluid flows in a dialysing fluid circuit through the dialysing fluid chamber of the dialyser. The present invention further relates to a method for detecting complications during an extracorporeal blood treatment.

BACKGROUND OF THE INVENTION

In methods of chronic blood-cleaning therapy, for example in hemodialysis, hemofiltration, and hemodiafiltration blood is conveyed via an extracorporeal blood circuit. An arteriovenous fistula is often applied surgically as an access to the blood vessel system. The use of an implant is also possible.

Of importance to the functional capability of fistulas is their perfusion. If the fistula flow falls below a critical value, the risk of a fistula thrombosis then increases with the possible loss of the vascular access, which in dialysis treatment represents a considerable complication. If the fistula flow during the dialysis treatment is insufficient and smaller than the extracorporeal blood flow, local fistula recirculation occurs, whereby a fraction of the dialysed blood fed back to the fistula with the venous blood line is again fed to the dialyser via the arterial blood line. The fistula recirculation causes a significant reduction in the dialysis efficiency (F. Gotch, "Models to predict recirculation and its effects on treatment time in single-needle-dialysis", First Intl. Symposium on Single-Needle-Dialysis, S. Rignoir, R. Vanholder and P. Ivanovich, Cleveland, ISAO Press, 1984, page 305 ff.). The measurement of the quality of the vascular access is therefore regarded as an important means of quality assurance in dialysis treatment.

Apart from fistula recirculation, a small part of the blood with such vascular accesses always circulates directly via the patient's blood circulation to the vascular access without being able to participate in the metabolic process in the capillary systems. This type of recirculation is called cardiopulmonary recirculation and usually amounts to a few percent.

On account of their clinical importance, a number of methods are known for measuring the recirculation. The known methods are generally based on a measurement of a physical or chemical characteristic quantity of the blood, which is changed in the venous branch of the extracorporeal circuit. The physical or chemical characteristic quantity of the blood may be changed directly by manual intervention in the extracorporeal blood circuit or also indirectly by intervention in the dialysing fluid circuit.

A method for the measurement of recirculation referred to as thermodilution is known from the article by Krämer and Polaschegg in the EDTNA-ERCA Journal Vol. XIX, no. 2, pages 8-15, April 1993. With the known method, a brief drop in temperature is initiated in the dialysing fluid circuit, which is transferred to the venous branch of the extracorporeal blood circuit and leads to a detectable temperature jump in the arterial branch of the extracorporeal circuit when a recirculation occurs.

A known device for performing the method referred to as thermodilution has a temperature sensor arranged in the arterial branch and venous branch of the extracorporeal circuit. The venous temperature sensor is used to detect the temperature jump that is attributable to the drop in temperature produced in the dialysing fluid circuit. The measured temperature jump is integrated over time and subsequently compared with the temperature course recorded in the arterial measuring sensor. The ratio of the two temperature integrals with respect to one another is a measure of the overall reduction in efficiency of the dialysis treatment due to fistula and cardiopulmonary recirculation.

The known device for the measurement of recirculation has been tried and tested in practice. A decisive drawback, however, lies in the fact that the recirculation is determined on the basis of a measured change in a physical or chemical characteristic quantity of the blood in the blood circuit. This is disadvantageous inasmuch as temperature sensors have to be arranged in the blood circuit. A relatively high outlay on equipment is thus incurred. Furthermore, the measurement with the temperature bolus requires a relatively long time. The recirculation measurement with the temperature bolus is therefore not carried out continuously during the treatment, but often only upon manual request.

German patent document DE 197 02 441 shows the drawbacks of the method referred to as thermodilation. In order to reduce the equipment outlay for the extracorporeal blood treatment apparatus, German patent document DE 197 02 441 proposes a method for determining the recirculation on the basis of the change in a physical or chemical characteristic quantity in the dialysing fluid upstream of the dialyser and detecting the change in a physical or chemical characteristic quantity in the dialysing fluid downstream of the dialyser.

Apart from the recirculation measurement, various methods are known for measuring the dialysance or clearance, which are criteria for the efficiency of a dialysis treatment. U.S. Pat. No. 6,702,774 describes a method for measuring dialysance or clearance during an extracorporeal blood treatment. In contrast with the method for measuring recirculation known as thermodilution, the determination of the dialysance or clearance takes place on the basis of a measured physical or chemical characteristic quantity of the dialysing fluid in the dialysing fluid circuit. A measurement in the extracorporeal blood circuit is not therefore required.

With the known methods, a physical or chemical characteristic quantity of the dialysing fluid is changed in a preset time interval upstream of the dialyser and the change in the physical or chemical characteristic quantity is measured downstream of the dialyser. The physical or chemical characteristic quantity is preferably the ion concentration of the dialysing fluid, which is determined by a conductivity measurement of the dialysing fluid. The dialysance is determined solely from the quantities on the dialysing fluid side from the integral over time of the measured dialysing fluid ion concentration upstream of the dialyser and the integral over time of the measured ion concentration downstream of the dialyser.

German patent document DE 197 47 360 A1 describes a method for determining the dialysance and clearance, wherein a predetermined quantity of a substance is added as a bolus to the dialysing fluid upstream of the dialyser, the dialysance of which substance is to be determined. The quantity of substance not dialysed in the dialyser is determined over time by integration of the substance concentration measured with a sensor downstream of the dialyser and the dialysance is ascertained from the added quantity of substance, the quantity of substance detected downstream of the dialyser and the dialysing fluid flow. German patent document DE 197

47 360 A1 mentions as the prior art the method described in German patent document DE 39 38 662, with which only the effective clearance, but not the dialyser clearance may be measured, whereby a distinction between the two values is to be made by the influence of the recirculation.

SUMMARY OF THE INVENTION

An aspect of the present invention is to provide a device with which complications may be detected with a high degree of reliability during an extracorporeal blood treatment.

A further aspect of the present invention is to provide a method that enables the detection of complications with a high degree of reliability during an extracorporeal blood treatment.

The example devices and methods according to the present invention are based on the combination of monitoring the dialysance or clearance on the basis of measured quantities on the dialysate side and monitoring the recirculation on the basis of measured quantities on the blood side. During the blood treatment, the dialysance or clearance is monitored at successive points in time on the basis of measurements on the dialysate side, without intervention into the extracorporeal blood circuit being required. The monitoring of the recirculation on the basis of measurements on the blood side only takes place when a change in the dialysance or clearance has been established.

The example devices and the methods according to the present invention are based on the knowledge that a recirculation is connected with a change, in particular a reduction, in the dialysance or clearance. On the other hand, a reduction in the dialysance or clearance may also be attributable to complications other than that of a recirculation. In the case of the example devices and the methods according to the present invention, a second measurement is therefore made after a change in the dialysance or clearance has been ascertained in order to check whether the cause of the change actually lies in the occurrence of a recirculation.

Since the recirculation measurement on the basis of the quantities on the blood side only takes place when such a complication is assumed, the monitoring on the basis of the quantities on the dialysing fluid side may be carried out continuously or virtually continuously.

The high degree of reliability of the example methods according to the present invention is explained by the fact that the conclusion is drawn that there is a recirculation only when two measuring procedures independent of one another indicate this.

The example devices and the methods according to the present invention make it possible to distinguish between complications attributable to a recirculation, for example complications with the vascular access, or complications that have other causes leading to a change in dialysance or clearance, for example a reduced efficiency of the dialyser.

According to an example embodiment, an example device according to the present invention has an evaluation device which, when complications occur, generates a control signal for an alarm or an intervention into the machine control of the treatment apparatus. The evaluation device preferably generates a first control signal, which indicates the change in the dialysance or clearance on account of a recirculation, and a second control signal, which indicates a change in the dialysance that is not the consequence of a recirculation.

In an example embodiment of the invention, the evaluation device has a memory unit for storing a preset value of a dialysance, clearance or recirculation and a comparison unit for comparing the dialysance, clearance or recirculation value ascertained at a specified time with the preset value. A change in the recirculation is established if the difference between the preset value and the value ascertained at a specified time is greater than a preset threshold value. The preset value may be an absolute value or the value ascertained in a preceding measurement.

The determination of the recirculation on the basis of the quantities on the blood side preferably takes place with the method referred to as thermodilution, which is known from the EDTNA-ERCA journal mentioned hereinabove, which is hereby incorporated by reference in its entirety. The determination of the dialysance or clearance preferably takes place according to the method known from U.S. Pat. No. 6,702,774 mentioned hereinabove, which is hereby incorporated by reference in its entirety.

In principle, however, other methods may also be used, as long as the continuous or virtually continuous measurement takes place only on the basis of quantities on the dialysate side and the measurement carried out solely upon the assumption of a complication takes place on the basis of quantities on the blood side.

An example device according to the present invention may form an independent unit, which is made available for a blood treatment apparatus. Since, however, the main components of the device according to the present invention as such, which include in particular the circuit components for the measurement and evaluation, e.g. temperature and conductivity sensors, microprocessors etc., are already generally present in the known blood treatment apparatuses, the example device according to the present invention may also be integrated into the blood treatment apparatus without high additional expenditure.

An example embodiment of the present invention is explained in greater detail below by reference to the drawings.

DETAILED DESCRIPTION OF THE DRAWINGS

Figure 1:
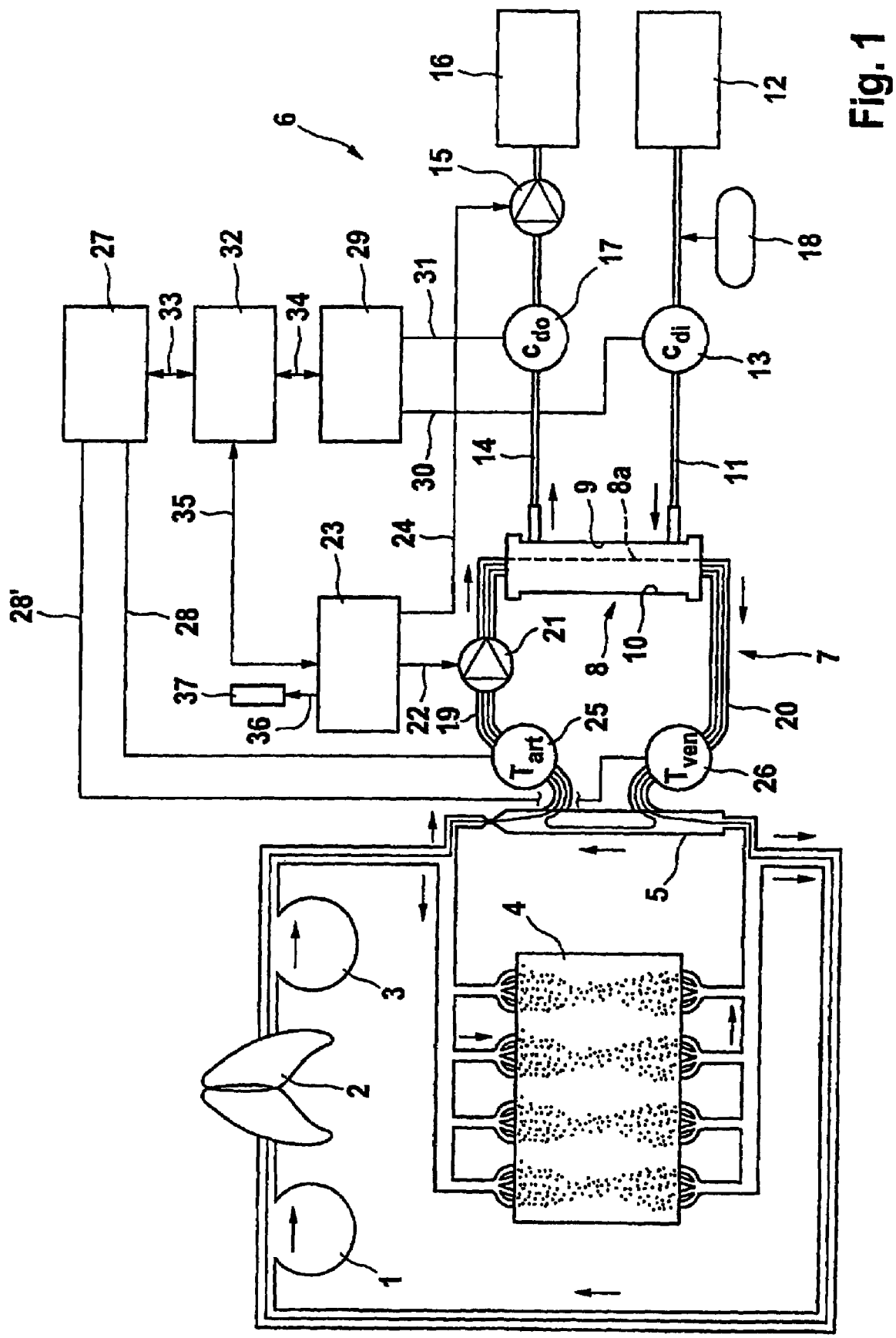
FIG. 1 shows a diagrammatic representation of the main components of an example apparatus for extracorporeal blood treatment with a device for detecting complications during the blood treatment.

The example device according to an example embodiment of the present invention is described below together with the main components of a dialysis apparatus including the intracorporeal circuit. However, other example devices according to the present invention may be formed as separate modules.

The intracorporeal circuit comprises right ventricle 1 of the heart, lungs 2, left ventricle 3 and all the capillary systems 4 of the body in internal organs, muscular systems and skin etc. In order to provide an access to the blood vessel system, an arteriovenous fistula 5 is applied.

The dialysis apparatus has a dialysing fluid circuit 6 and an extracorporeal blood circuit 7, between which there is located a dialyser 8 with a dialysing fluid chamber 9 and a blood chamber 10, which are separated from one another by a semipermeable membrane 8a.

Dialysing fluid chamber 9 is connected upstream of dialyser 8 via a dialysing fluid supply line 11 to a dialysing fluid source 12. A measuring device 13 with a conductivity sensor or an optical sensor for determining dialysing fluid input concentration $c_{di}$ is incorporated into the dialysing fluid supply line. Connected to dialysing fluid chamber 9 downstream of dialyser 8 is a dialysing fluid discharge line 14, which has a dialysing fluid pump 15 and which leads to a drain 16. A measuring device 17 with a conductivity sensor or an optical sensor for determining the dialysing fluid output concentration $c_{do}$ is incorporated into dialysing fluid discharge line 14.

A device arranged upstream of dialyser 8 is designated by reference number 18, with which device a physical or chemical characteristic quantity of the dialysing fluid flowing into the dialyser may be changed, in particular a bolus of a substance, i.e. a concentrate bolus, may be delivered.

Extracorporeal blood circuit 7 comprises an arterial branch 19, which is connected to the arterial part of fistula 5, blood chamber 10 of dialyser 8 and a venous branch 20, which is connected to the venous part of the fistula. Arranged in arterial branch 19 is a blood pump 21, which is connected via a control line 22 to a control unit 23, with which the delivery rate of blood pump 21 may be changed. Control unit 23 is connected via a further control line 24 to dialysing fluid pump 15.

A measuring device 25 for measuring the arterial blood temperature is incorporated into arterial branch 19 of extracorporeal blood circuit 7 and a measuring device 26 for measuring the venous blood temperature is incorporated into the venous branch.

The example device according to the example embodiment of the present invention has a first and second device for monitoring the recirculation. First monitoring device 27 receives, via signal lines 28, 28', the measured values of the arterial and venous blood temperature measured by arterial and venous measuring device 25, 26. Second monitoring device 29 receives via signal lines 30, 31 measured values $c_{di}$, $c_{do}$ of measuring devices 13, 17 for the ion concentration upstream and downstream of the dialyser.

An evaluation device 32 receives via data lines 33, 34 the data acquired in monitoring devices 27, 29. Evaluation device 32 is connected by a further data line 35 to control unit 23. An acoustic and/or optical display or alarm device 37 is connected via a signal line 36 to control unit 23.

With device 18, it is possible not only to produce a concentrate bolus on the dialysing fluid side, but also a temperature bolus on the blood side. For this purpose, device 18 briefly raises the temperature of the dialysing fluid flowing into the dialysing fluid chamber, as a result of which the temperature of the blood flowing in the opposite direction out of the blood chamber is also briefly raised.

The function of the device and the principle of the measurement will be explained in detail below.

The blood emitted from left ventricle 1 flows for the most part into the capillary systems of all the organs, to a small extent into fistula 5. In the event that the blood flow in extracorporeal circuit 7 is smaller than the blood flow of the blood flowing into the fistula and out of the fistula, the fistula blood flows partly through extracorporeal circuit 7, and partly through fistula 5.

If the extracorporeal blood flow is greater than the fistula flow, blood from the extracorporeal circuit recirculates, whereby there is a flow through the fistula from the venous to the arterial connection. The venous blood, the blood flowing through the fistula and the blood coming from the capillary systems finally unites again in the return flow to the heart.

The first device for monitoring recirculation 27, which is connected to control unit 23, initiates the measurement by the fact that device 18 produces a temperature bolus. Dialyser 8, the dialysing fluid rate of which is higher than the blood flow rate, and whose dialysing fluid flows in the opposite direction to the blood, transfers temperature bolus $T_{Dia}$ to the blood at the outlet of blood chamber 10. Temperature bolus $T_{ven}$ in venous branch 20 of extracorporeal blood circuit 7 is measured by venous measuring device 26. The temperature bolus then spreads along the two recirculation paths and is reduced in its height at the points at which the flow is mixed. A smaller response bolus $T_{art}$ is then measured by arterial measuring device 25. First monitoring device 27 calculates the ratio of the measured arterial and venous temperature bolus. This ratio is equal to the total recirculation, i.e. the sum of the fistula and cardiopulmonary recirculation.

Figure 2:
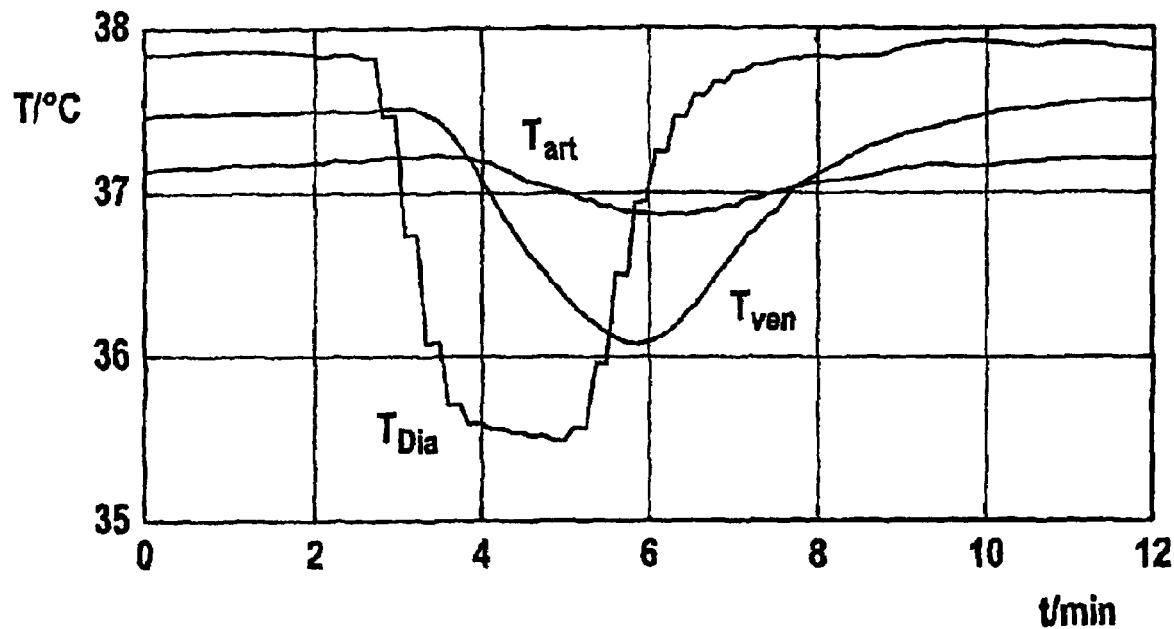
FIG. 2 shows the time-related course of the temperature of the blood in the arterial and venous branch of the extracorporeal blood circuit after a temperature bolus on the dialysate side.

FIG. 2 shows the temperature courses described above. The dialysate temperature is lowered for 2.5 min by 2.5° to produce the bolus. With a delay, venous blood temperature $T_{ven}$ is influenced thereby. Arterial response bolus $T_{art}$ is observed after a further short delay. In the example of FIG. 2, a total recirculation of 22% results from the ratio of the bolus height.

Second device 29 for monitoring the recirculation initiates, at the start of the measurement with device 18, a brief increase in the ion concentration of the dialysing fluid flowing into dialysing fluid chamber 9 of dialyser 8, which is measured by measuring device 13. The change in the ion concentration of the dialysing fluid flowing out of the dialysing fluid chamber attributable to the concentrate bolus is measured by measuring device 17.

Figure 3:
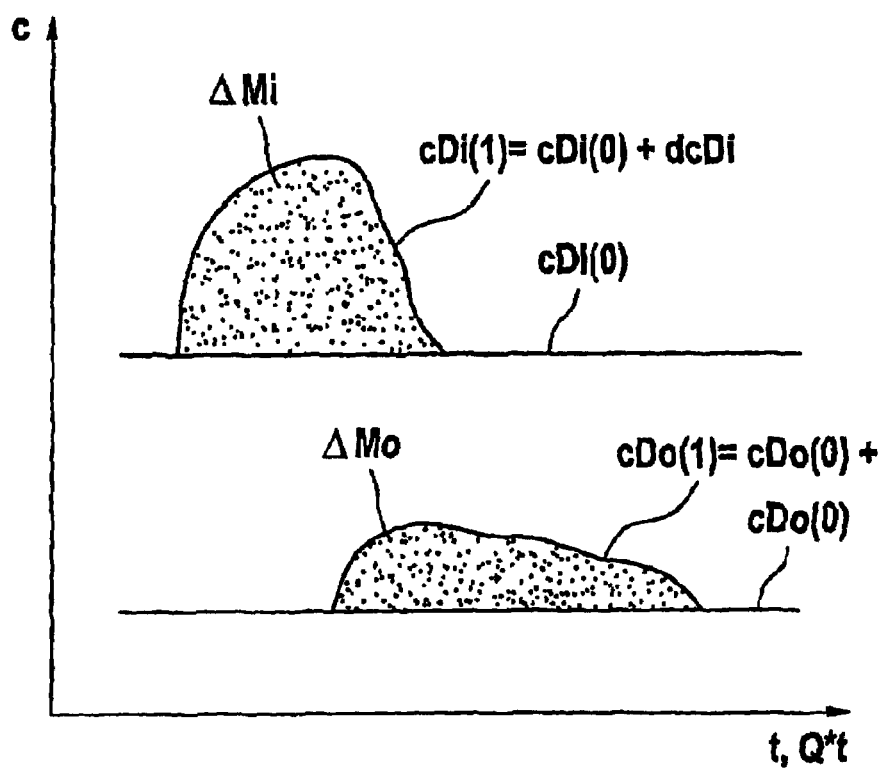
FIG. 3 shows the time-related course of the measured ion concentration of the dialysing fluid upstream and downstream of the dialyser after a concentration bolus.

FIG. 3 shows the time-related course of the change in the dialysing fluid input and output concentration $C_{di}$ and $C_{do}$. It is evident that the concentrate bolus at the input of the dialyser occurs with a time delay at the output of the dialyser. The amplitude of the concentrate bolus at the output is smaller than at the input of the dialyser. Only the part of the concentrate bolus that is not attributable to a basic or fundamental concentration is to be taken into account here. Measured values before and/or after the bolus may be used to determine the basic concentration.

Second monitoring device 29 has a computing unit, which calculates, from the time-related course of the dialysing fluid ion concentration upstream and downstream of the dialyser and from the dialysing fluid rate $Q_d$, which is preset by control unit 23 and corresponds to the flow rate of dialysing fluid pump 15, the two quantities $\Delta M_i$ and $\Delta M_o$ according to the following equations:

$$\Delta Mi = Qd * \int dcdi * dt \qquad (1)$$

$$\Delta Mo = Qd * \int dcdo * dt. \qquad (2)$$

Dialysance D is calculated from the quantities $\Delta M_i$ and $\Delta M_o$ according to the following equation:

$$D = QD * \frac{\Delta Mi - \Delta Mo}{\Delta Mi}. \qquad (3)$$

During the dialysis treatment, second monitoring device 29 continuously performs measurements to determine the dialysance at specified times. The values of the dialysance are evaluated in evaluation device 32.

Evaluation device 32 has a memory unit for storing a preset value of the dialysance, for example a specific dialysance value for an effective dialysis treatment, and a comparison unit for comparing the ascertained dialysance value with the preset dialysance value. If the difference between the preset value and the ascertained value is greater than a preset threshold value, for example a percentage deviation of more than 10 to 30%, preferably 15%, first monitoring device 27 is automatically activated.

If the dialysance has diminished by more than the preset amount, first monitoring unit 27 performs a measurement of the recirculation. The ascertained value of the recirculation is compared with a preset recirculation value, which is also stored in the memory unit. The preset dialysis and recirculation values may also be filed on a patient chart specific to the patient.

If the amount of the difference between the preset recirculation value and the ascertained recirculation value is greater than a preset threshold value, for example if the recirculation has increased by more than 10 to 30%, preferably 20%, a first control signal is generated, if the difference is smaller than the preset threshold value, for example if the recirculation has not changed or has changed only slightly, a second control signal is generated. The two control signals are received by control unit 23 in order that appropriate measures may be initiated.

Provision may be made such that an intervention is made into the machine control. Moreover, alarm or display device 37 may be triggered, which signals that either a complication has occurred that is attributable to the dialyser or to the vascular access.

A defective vascular access is assumed when a significant reduction in the dialysance or clearance is ascertained with first monitoring device 29 and a significant reduction in the recirculation is ascertained with second monitoring device 27.

The invention claimed is:

1. A detecting device for detecting complications during an extracorporeal blood treatment with a blood treatment apparatus, wherein the blood to be treated flows in an extracorporeal blood circuit through the blood chamber of a dialyser, said dialyser being divided by a semipermeable membrane into the blood chamber and a dialysing fluid chamber, and a dialysing fluid flows in a dialysing fluid circuit through the dialysing fluid chamber of the dialyser, the detecting device comprising:
   a device for changing a physical or chemical characteristic quantity of the blood in the extracorporeal blood circuit;
   a device for changing a physical or chemical characteristic quantity of the dialysing fluid in the dialysing fluid circuit;
   at least one first measuring device for measuring a physical or chemical characteristic quantity of the blood;
   at least one second measuring device for measuring a physical or chemical characteristic quantity of the dialysing fluid;
   a first monitoring device for monitoring the recirculation of the blood treatment, the first monitoring device configured to cooperate with the device for changing a physical or chemical characteristic quantity of the blood and the at least one first measuring device for measuring a physical or chemical characteristic quantity of the blood when activated in such a way that the recirculation can be monitored on the basis of a change in the measured physical or chemical characteristic quantity of the blood;
   a second monitoring device configured to monitor the dialysance or clearance of the blood treatment, the second monitoring device configured to cooperate with the device for changing a physical or chemical characteristic quantity of the dialysing fluid and the at least one second measuring device for measuring a physical or chemical characteristic quantity of the dialysing fluid in such a way that the dialysance or clearance can be monitored on the basis of a change in the measured physical or chemical characteristic quantity of the dialysing fluid, wherein the second monitoring device is further configured to monitor the recirculation on the basis of ascertaining the change in the dialysance or clearance, and
   an evaluation device configured to cooperate with the first monitoring device and the second monitoring device to determine the recirculation in such a way that, during the blood treatment, the second monitoring device is configured to be activated at successive points in time, wherein the first monitoring device is configured to be activated after ascertainment of the change in the recirculation with the second monitoring device, so that the occurrence of a complication can be detected.

2. The device according to claim 1, wherein the evaluation device comprises a device for generating a control signal when a complication occurs.

3. The device according to claim 2, wherein the device for generating a control signal is configured to generate a first control signal when, after ascertainment of a change in the recirculation with the second monitoring device, the first monitoring device ascertains a change in the recirculation.

4. The device according to claim 3, further comprising a device for generating an alarm when the first control signal is generated and/or for performing an intervention in the machine control of the blood treatment apparatus when the first control signal is generated.

5. The device according to claim 2, wherein the device for generating a control signal is configured to generate a second control signal when, after the second monitoring device ascertains a change in the recirculation, the first monitoring device does not ascertain a change in the recirculation.

6. The device according to claim 5, further comprising a device for generating an alarm when the second control signal is generated and/or for performing an intervention in the machine control of the blood treatment apparatus when the second control signal is generated.

7. The device according to claim 1, wherein the evaluation device comprises a memory unit for storing a preset value of the dialysance or clearance or recirculation and a comparison unit for comparing the dialysance, clearance or recirculation value ascertained at a specified time with the preset value, wherein a change in the recirculation, dialysance or clearance can be ascertained if the amount of the difference between the preset value and the value ascertained at a specified time is greater than the preset threshold value.

8. The device according to claim 1, wherein the first monitoring device comprises a device for changing the temperature of the blood and a device for measuring the temperature of the blood in the blood circuit.

9. The device according to claim 1, wherein the second monitoring device comprises a device for changing the concentration of a substance in the dialysing fluid and a device for measuring the concentration of the substance in the dialysing fluid in the dialysing fluid circuit.

10. A blood treatment apparatus, comprising:
    a dialyser divided by a semipermeable membrane into a blood chamber and a dialysing fluid chamber, wherein the blood chamber is incorporated into an extracorporeal blood circuit and the dialysing fluid chamber of the dialyser is incorporated into a dialysing fluid circuit, and a detecting device comprising:

a device for changing a physical or chemical characteristic quantity of the blood in the extracorporeal blood circuit, a device for changing a physical or chemical characteristic quantity of the dialysing fluid in the dialysing fluid circuit, at least one first measuring device for measuring a physical or chemical characteristic quantity of the blood;

at least one second measuring device for measuring a physical or chemical characteristic quantity of the dialysing fluid, a first monitoring device for monitoring the recirculation of the blood treatment, the first monitoring device configured to cooperate with the device for changing a physical or chemical characteristic quantity of the blood and the at least one first measuring device for measuring a physical or chemical characteristic quantity of the blood when activated in such a way that the recirculation can be monitored on the basis of a change in the measured physical or chemical characteristic quantity of the blood, a second monitoring device configured to monitor the dialysance or clearance of the blood treatment, the second monitoring device configured to cooperate with the device for changing a physical or chemical characteristic quantity of the dialysing fluid and the at least one second measuring device for measuring a physical or chemical characteristic quantity of the dialysing fluid in such a way that the dialysance or clearance can be monitored on the basis of a change in the measured physical or chemical characteristic quantity of the dialysing fluid, wherein the second monitoring device is further configured to monitor the recirculation on the basis of ascertaining the change in the dialysance or clearance, and an evaluation device configured to cooperate with the first monitoring device and the second monitoring device to determine the recirculation in such a way that, during the blood treatment, the second monitoring device is configured to be activated at successive points in time, wherein the first monitoring device is configured to be activated after ascertainment of the change in the recirculation with the second monitoring device, so that the occurrence of a complication can be detected.

11. The detecting device of claim 1, wherein the at least one second measuring device further comprises:

a measuring device for measuring a physical or chemical characteristic quantity of the dialysing fluid in a dialysis fluid supply line of the dialysis fluid circuit; and a measuring device for measuring a physical or chemical characteristic quantity of the dialysing fluid in a dialysis fluid discharge line of the dialysis fluid circuit.

12. The detecting device of claim 11, wherein the at least one first measuring device further comprises:

a measuring device for measuring a physical or chemical characteristic quantity of the blood in a venous branch of the extracorporeal blood circuit; and a measuring device for measuring a physical or chemical characteristic quantity of the blood in an arterial branch of the extracorporeal blood circuit.

13. The detecting device of claim 11, wherein the at least one second measuring device measures concentration.

14. The detecting device of claim 12, wherein the at least one first measuring device measures temperature.

* * * * *